United States Patent [19]

Kroll

[11] Patent Number: 6,007,395

[45] Date of Patent: Dec. 28, 1999

[54] SUN TANNING LIFE VEST

[76] Inventor: Mark W. Kroll, 651 Carnellon Ct., Simi Valley, Calif. 93065

[21] Appl. No.: 08/927,243

[22] Filed: Sep. 11, 1997

[51] Int. Cl.[6] .................................................. B63C 9/08
[52] U.S. Cl. ......................................... 441/106; 441/112
[58] Field of Search ................................... 441/102, 108, 441/106, 111, 112, 114–120; 428/135, 229

[56] References Cited

U.S. PATENT DOCUMENTS 2,521,205  9/1950  David ..................................... 441/102
4,546,493  10/1985  Bortnick ................................. 428/229
4,891,855  1/1990  Cheng-Chung et al. .
5,518,798  5/1996  Riedel .................................... 428/135

FOREIGN PATENT DOCUMENTS 2540355  8/1984  France .

Primary Examiner—Jesus D. Sotelo

[57] ABSTRACT

A life vest for water sports is taught which is translucent to ultraviolet radiation. This allows the wearer to achieve a uniform tan without having the harsh tan lines where the edges of a life vest would normally be. This allows an individual to enjoy both safety and tanning without having to make a choice between the two.

20 Claims, 3 Drawing Sheets

SUN TANNING LIFE VEST

BACKGROUND OF THE INVENTION

People are encouraged to wear life jackets when they are engaged in water sports such as water skiing, boating or jet skiing. However, the same individuals are usually interested in an even suntan. When someone wears a traditional lifejacket the area under the life jacket receives no tan and the other areas are very darkly tanned leaving embarrassing lines between the two regions.

Clothing, especially bathing suits, is now available that allows the passage of ultraviolet radiation to facilitate a full body suntan. However, no one has taught a lifevest that will transmit ultraviolet rays to give an even tan. Cheng-Chung (U.S. Pat. No. 4,891,855) teaches a floating air mattress with a transparent top layer.

DETAILED DESCRIPTION OF THE PREFERRED EMBODIMENT

Figure 1:
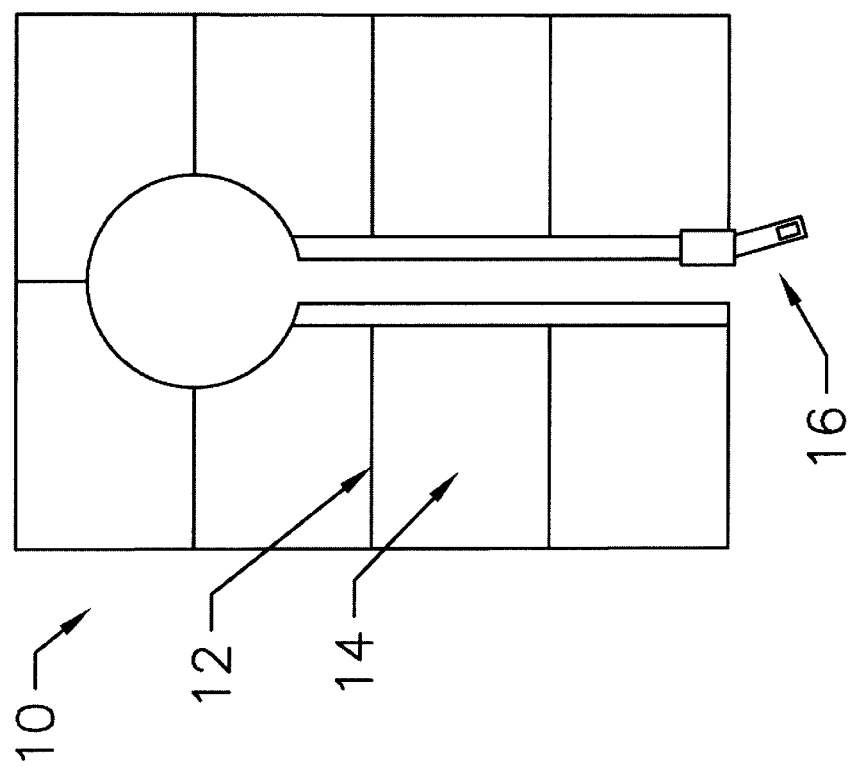
FIG. 1 shows an embodiment of the invention which is continuously inflated.

FIG. 1 shows one embodiment of the present invention. Here a life vest 10 is made using a film that is translucent to ultraviolet light. A good example of such a film is polyvinylidene fluoride. PVDF is distinctive among polymers in that rather than degrading from ultraviolet light it actually gets stronger by cross linking. An oriented PVDF film is a good transmitter of ultraviolet (UV) light and can have transmittance as high as 85%–90%.

Other materials to consider would be Ecdel from Eastman Chemical Company of Tennessee, TPX of Mitsui Plastic's Inc. of Japan, Teflon of DuPont Engineering Polymers, and Tenite of Eastman Chemical Company of Tennessee.

The life vest is made by having vertical separating walls 12 into chambers 14. Each chamber 14 is filled with ultraviolet transmitting gas such as carbon dioxide or air or nitrogen among many others.

A molded plastic zipper 16 is used to secure the vest to the subject. Other methods of securement could be used as well. Straps to go around the back or through the crotch would also be acceptable. They preferably would be made of a oriented PVDF or other UV transmissive material.

The vest in FIG. 1 shows one embodiment for an over-the-neck type of life jacket. The same idea of the invention could easily be applied to a traditional vest type that goes all around the back without departing from the spirit of the invention.

Figure 2:
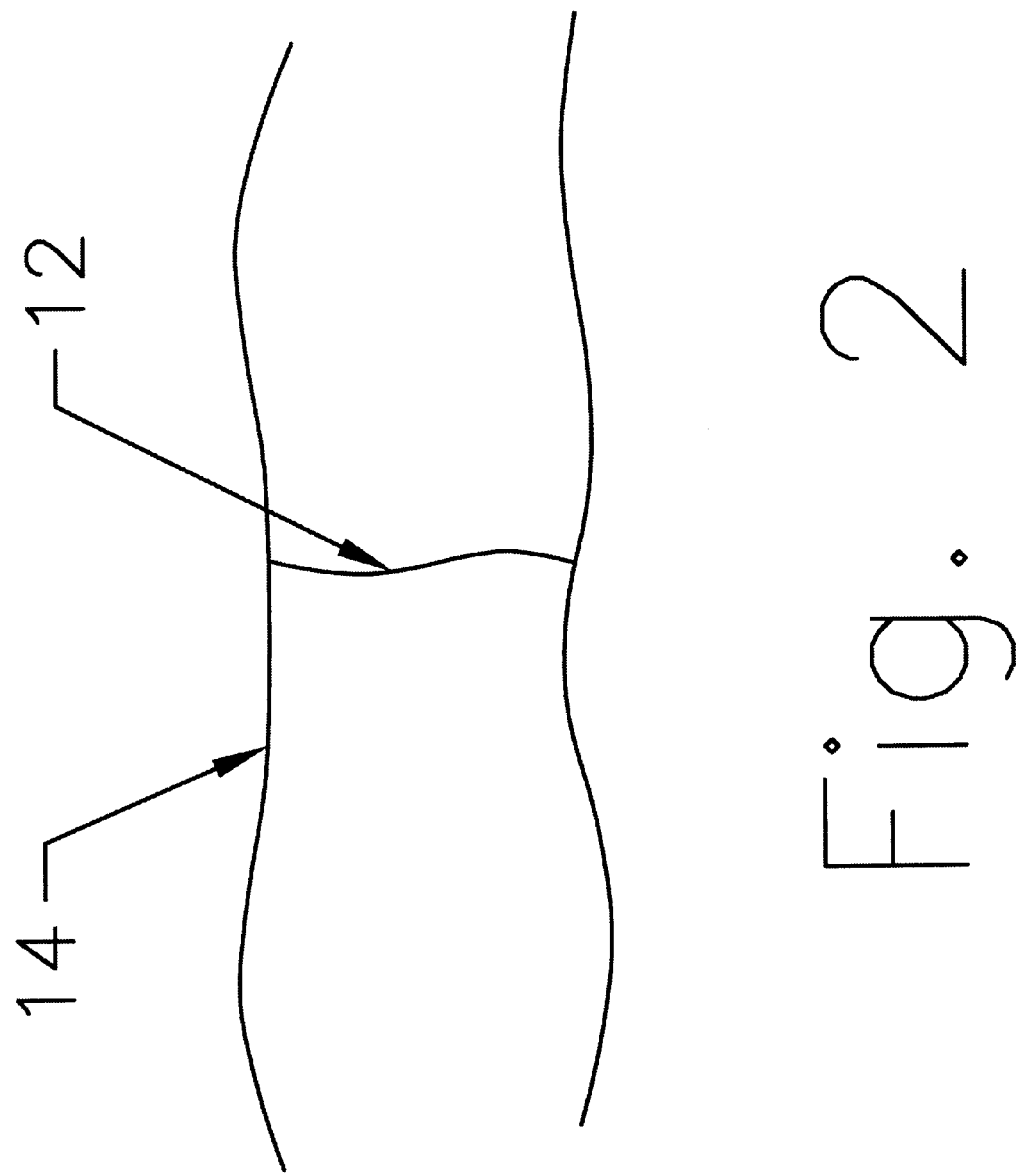
FIG. 2 shows the side view of the continuously inflated embodiment.

FIG. 2 shows the side view of the cells in the invention as shown in FIG. 1. Here walls 12 again are separating the vest and the chambers 14 each filled with the inert gas.

Figure 3:
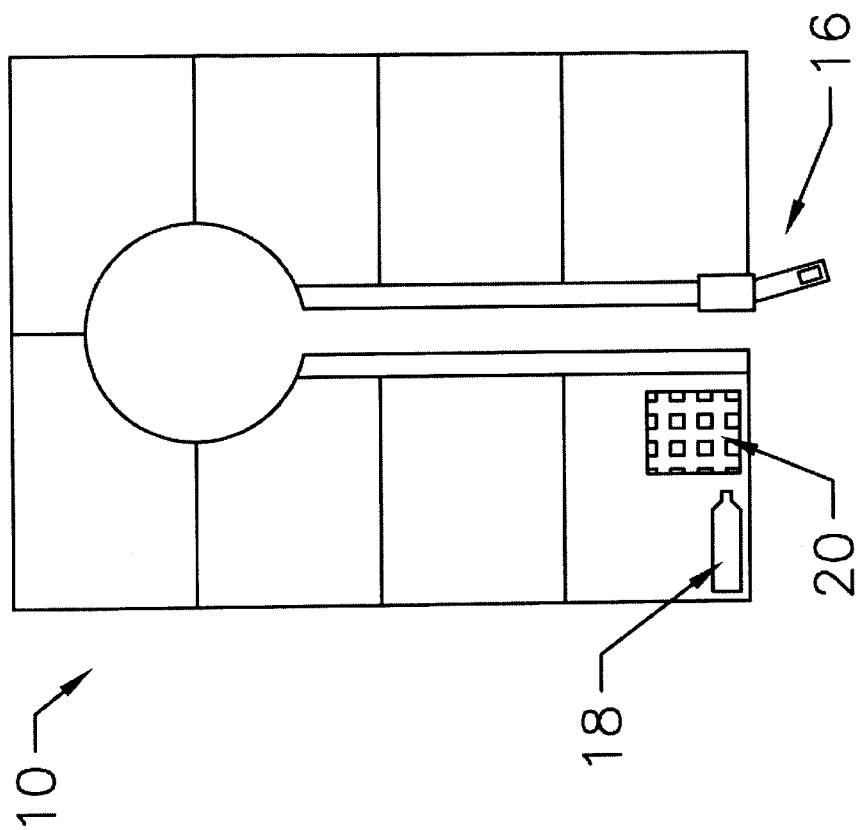
FIG. 3 shows a plan view of the acutely inflating embodiment of the invention.

FIG. 3 shows an embodiment of the present invention that inflates only in response to water immersion. This "acute" embodiment uses a compressed carbon dioxide reservoir 18 which is triggered by water sensor 20 to release the carbon dioxide into the vest to inflate it. Other compressed gasses could be used as well.

This vest would be very comfortable and lightweight for subjects and yet would inflate instantly upon submersion in water.

Even if the material is not 100% transmissive to the ultraviolet light, one can match the transmission by using the appropriate degree of sunblock on the exposed limbs. For example one might use a 4 or 6 level sunblock on the arms to avoid having a contrast in tans.

I claim:

1. A buoyant body conforming apparatus comprising:
    a vest member having at least one enclosed chamber defined by an outer surface, said outer surface being made of a film material which is at partially transmissive to ultraviolet light, said at least one enclosed chamber being adapted such that it may be filled with a gas which is transmissive to ultraviolet light; and
    means for releasably securing said vest member to the torso of a wearer of said buoyant body conforming apparatus when said vest member is filled with a gas which is transmissive to ultraviolet light, whereby said gas-filled vest member transmits ultraviolet light therethrough in order to allow suntanning of the torso of the wearer of said buoyant body conforming apparatus while simultaneously providing positive buoyancy to the wearer of said buoyant body conforming apparatus for water safety.

2. The buoyant body conforming apparatus of claim 1 in which the gas which said vest member is filled with is air.

3. The buoyant body conforming apparatus of claim 1 in which the gas which said vest member is filled with comprises carbon dioxide.

4. The buoyant body conforming apparatus of claim 1 in which the gas which said vest member is filled with comprises nitrogen.

5. The buoyant body conforming apparatus of claim 1 in which said at least one enclosed chamber of said gas-filled vest member is made of a polymer film material which is at partially transmissive to ultraviolet light and which will not be significantly degraded by ultraviolet light.

6. The buoyant body conforming apparatus of claim 5 in which said polymer film material comprises polyvinylidene fluoride.

7. The buoyant body conforming apparatus of claim 5 in which said polymer film material comprises Ecdel.

8. The buoyant body conforming apparatus of claim 5 in which said polymer film material comprises TPX.

9. The buoyant body conforming apparatus of claim 5 in which said polymer film material comprises Teflon.

10. The buoyant body conforming apparatus of claim 5 in which said polymer film material comprises Tenite.

11. The buoyant body conforming apparatus of claim 5 in which said polymer film material transmits at least 85% of ultraviolet light.

12. The buoyant body conforming apparatus of claim 5 in which said polymer film material transmits ultraviolet light at a level equivalent to a sun protection factor (SPF) of between approximately 4 and 6.

13. The buoyant body conforming apparatus of claim 1 in which said means for releasably securing said vest member to the torso of a wearer of said buoyant body conforming apparatus comprises a zipper attaching two sides of said vest member together.

14. The buoyant body conforming apparatus of claim 13 in which said means for releasably securing said vest member to the torso of a wearer of said buoyant body conforming apparatus comprises a molded plastic zipper attaching said two sides of said vest member together.

15. The buoyant body conforming apparatus of claim 1 in which the apparatus is normally deflated, said buoyant body conforming apparatus additionally comprising:

means for rapidly inflating said vest member.

16. The buoyant body conforming apparatus of claim 15 in which said means for rapidly inflating said vest member comprises:

a compressed carbon dioxide reservoir; and water sensor means for releasing carbon dioxide from said compressed carbon dioxide reservoir to rapidly inflate said vest member in response to the detection of the presence of water.

17. The buoyant body conforming apparatus of claim 1 in which vest member has a plurality of enclosed chambers each defined by an outer surface made of a film material which is at partially transmissive to ultraviolet light, each adjacent pair of said enclosed chambers being separated by a wall member made of a film material which is at partially transmissive to ultraviolet light, said enclosed chambers each being filled with a gas which is transmissive to ultraviolet light.

18. The buoyant body conforming apparatus of claim 1 in which said film material is impermeable to gas to thereby retain gas contained in said at least one enclosed chamber therein.

19. An inflatable life vest comprising:

a vest member having at least one enclosed chamber defined by an outer surface, said outer surface being made of an ultraviolet transmissive film material, said at least one enclosed chamber being adapted such that it may be filled with a gas which is transmissive to ultraviolet light; and means for releasably securing said vest member to the torso of a wearer of said buoyant body conforming apparatus when said vest member is filled with a gas which is transmissive to ultraviolet light, whereby said gas-filled vest member transmits ultraviolet light therethrough in order to allow suntanning of the torso of the wearer of said buoyant body conforming apparatus while simultaneously providing positive buoyancy to the wearer of said buoyant body conforming apparatus for water safety.

20. A buoyant body conforming apparatus comprising:

a wearable vest member comprising a plurality of enclosed chambers each of which enclosed chambers is defined by an outer surface, said wearable vest member being predominantly made of a film material which is transmissive to ultraviolet light, said plurality of enclosed chambers each being adapted such that they may be filled with a gas which is transmissive to ultraviolet light; and means for releasably securing said vest member to the torso of a wearer of said buoyant body conforming apparatus when said plurality of enclosed chambers of said vest member are filled with a gas which is transmissive to ultraviolet light, whereby said gas-filled vest member transmits ultraviolet light therethrough in order to allow suntanning of the torso of the wearer of said buoyant body conforming apparatus while simultaneously providing positive buoyancy to the wearer of said buoyant body conforming apparatus for water safety.

* * * * *